(12) United States Patent
Lenker et al.

(10) Patent No.: US 6,183,495 B1
(45) Date of Patent: Feb. 6, 2001

(54) WIRE FRAME PARTIAL FLOW OBSTRUCTION DEVICE FOR ANEURYSM TREATMENT

(75) Inventors: Jay Lenker, San Clemente; K. David Crockett, Los Angeles, both of CA (US)

(73) Assignee: Micro Therapeutics, Inc., Irvine, CA (US)

(*) Notice: Under 35 U.S.C. 154(b), the term of this patent shall be extended for 0 days.

(21) Appl. No.: 09/376,671

(22) Filed: Aug. 16, 1999

Related U.S. Application Data

(63) Continuation of application No. 08/850,311, filed on May 5, 1997, now Pat. No. 5,980,554.

(51) Int. Cl.[7] .................................................. A61M 29/00
(52) U.S. Cl. .................................................. 606/198
(58) Field of Search .................................. 606/191, 195, 606/198, 200; 623/1.15, 1.16, 1.35, 1.36, 12; 604/48, 52, 53, 93, 104, 106

(56) References Cited

U.S. PATENT DOCUMENTS

| | | | |
|---|---|---|---|
| 4,512,338 | 4/1985 | Balko et al. | 606/105 |
| 4,856,516 | 8/1989 | Hillstead | 606/194 |
| 4,913,141 | 4/1990 | Hillstead | 606/108 |
| 5,104,404 | * 4/1992 | Wolff | 623/1 |
| 5,466,242 | 11/1995 | Mori | 606/198 |
| 5,514,154 | * 5/1996 | Lau et al. | 606/195 |
| 5,540,701 | 7/1996 | Sharkey et al. | 606/153 |
| 5,554,181 | 9/1996 | Das | 623/1 |

* cited by examiner

Primary Examiner—Michael Buiz
Assistant Examiner—David O. Reip
(74) Attorney, Agent, or Firm—K. David Crockett, Esq.; Crockett & Crockett

(57) ABSTRACT

A wire frame stent or occluding device for use within the vasculature. The device can be stretched into a double wire or single wire configuration for easy deployment into the vasculature.

12 Claims, 6 Drawing Sheets

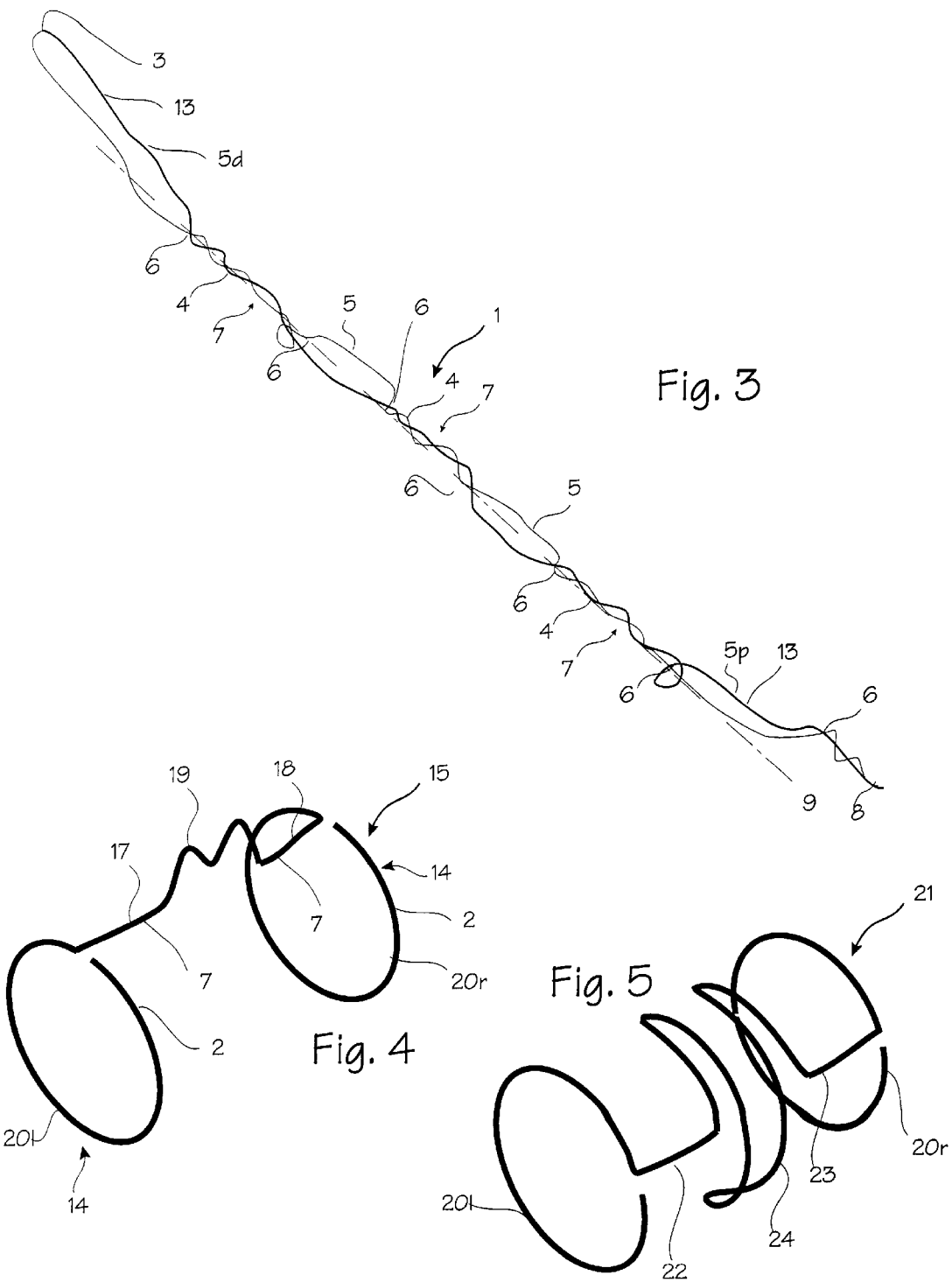

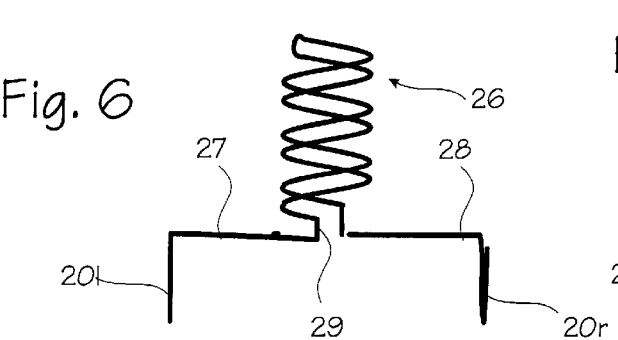
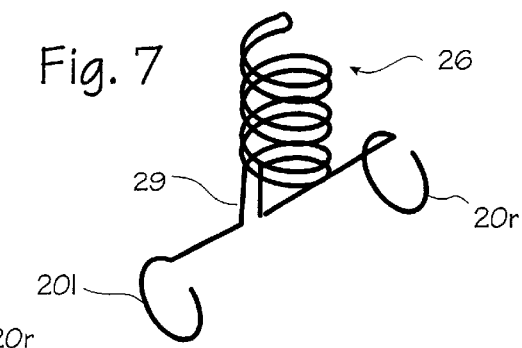
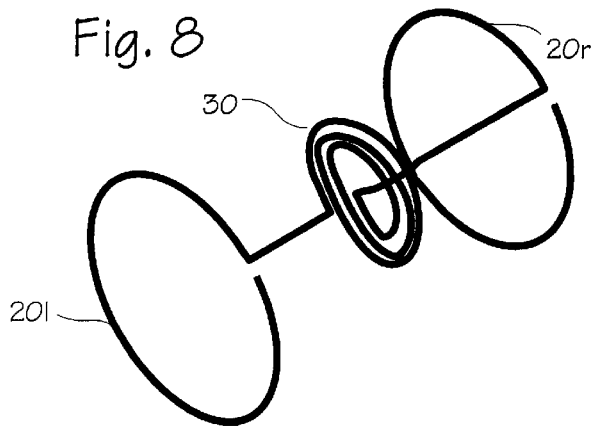
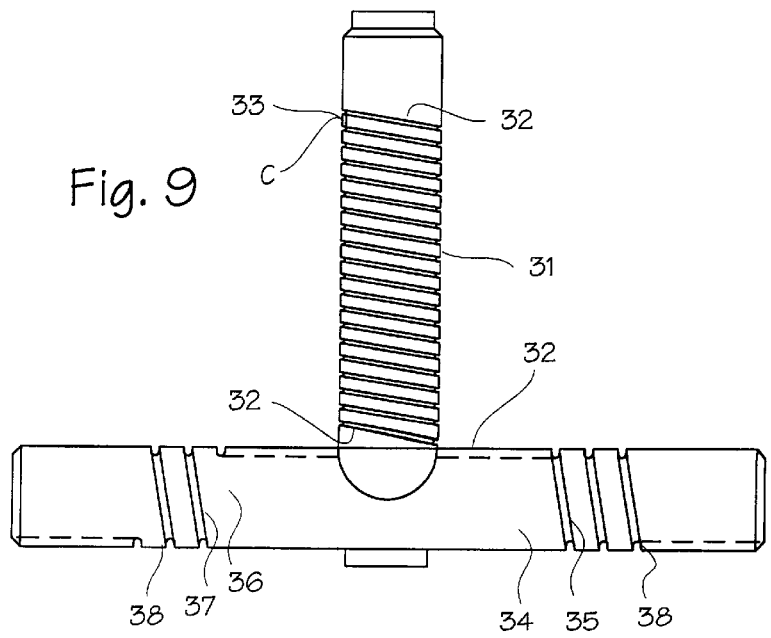

WIRE FRAME PARTIAL FLOW OBSTRUCTION DEVICE FOR ANEURYSM TREATMENT

This application is a continuation of U.S. patent application Ser. No. 08/850,311, filed May 5, 1997, now U.S. Pat. No. 5,980,554.

FIELD OF THE INVENTION

This invention relates to devices and methods for treatment of aneurysms.

BACKGROUND OF THE INVENTION

Aneurysms are a common defect in the vascular system that account for a wide range of symptoms. When they occur in the brain, aneurysms can cause stroke or death, as well as several well-known neurological defects such as loss of sight, hearing or balance. The treatment of aneurysms within the brain may be accomplished with a number of therapies currently available. Open surgical techniques require cutting into the skull and lifting brain matter away from the aneurysm so that the aneurysm may be accessed, clipped or sutured closed and cut away. These techniques are very risky, and are reserved until absolutely necessary because of high mortality and high chance of neurological defects caused by the operation itself.

The high risk and generally unsatisfactory results of open surgery on aneurysms (especially within the brain) have led researchers to develop techniques for treating aneurysms from inside the blood vessels. Endovascular and percutaneous insertion of devices avoids the danger of open surgery on the brain, but presents technical challenges. Grafts, stents and combinations of stents and grafts have been proposed for use in larger vessels such as the aorta and the peripheral arteries. The purpose of these devices is to close off the aneurysm from the circulatory system to prevent rupture and promote resorption of the mass of the aneurysm. These devices tend to be bulky and generally unsuitable for the small environment of the brain. Our co-pending U.S. patent application Ser. No. 08/707,996, filed Sep. 18, 1996 and U.S. Patent application No. 08/762110, filed Dec. 9, 1996 present several stent designs and stent delivery systems particularly suited to be used within the brain.

Another approach to treating aneurysms, suitable for treatment within the brain, is stuffing the aneurysm with foreign material to promote thrombus within the aneurysm and eventually eliminate the threat of ruptures and promote resorption of the aneurysm sac. As early as 1975, metal coils were successfully used to occlude the renal arteries. Gianturco, et al., Mechanical Devices for Arterial Occlusions, 124 Am. J. Roent. 428 (1975). The purpose of the coil is to encourage quick formation of a thrombus (a blood clot) around the coil. The coils are currently in use for a wide range of treatments, and are referred to variously as occlusive coils, embolization coils, or Gianturco coils. Embolization coils of appropriate size for placement within aneurysms are commercially available from Target Therapeutics, Inc. and Cook, Inc. Embolization coils made with electrolytic mechanisms for detachment from the delivery catheter are referred to as GDC's or Guglielmi Detachable Coils. The use of GDC's is illustrated, for example, in Klein, et al., Extracranial Aneurysms and Arteriovenous Fistula: Embolization with the Guglielmi Detachable Coil, 201 Radiology 489 (1996). Use of the GDC coils within the brain is illustrated, for example, in Casasco, et al., Selective Endovascular Treatment Of 71 Intracranial Aneurysms With Platinum Coils, 79 J. Neurosurgery 3 (1993).

Because Gianturco and Guglielmi coils are often used to occlude aneurysms in critical areas of the body, it is important that they remain in place where they are implanted. However, migration of the coils after placement is a common but dangerous problem encountered with these coils. Watanabe, Retrieval Of A Migrated Detachable Coil, 35 Neuro. Med. Clin. 247 (1995) reports the migration of a coil into the basilar artery from a placement in the superior cerebellar artery. Halbach, et al., Transarterial Platinum Coil Embolization Of Carotid Cavernous Fistulas, 12 AJNR 429 (1991) reports the migration of a coil from the internal carotid artery. Migration is particularly common with coils placed in wide neck aneurysms. The possible migration of coils is a danger that must be considered in every procedure, and actual migration can be life threatening complication, since embolization at an unwanted site could occlude a critical blood flow. Migration of the coil may also represent a failure of the intended therapeutic procedure.

Our co-pending U.S. patent application Ser. No. 08/813,614, filed Mar. 7, 1997, discloses a hoop stent for holding open blood vessels subject to occlusive disease. The stent, which is made of a single wire, and the delivery mechanism for the stent allow the stent to placed with a low profile by stretching the stent along its long axis rather than compressing it radially. A wide variety of other stent designs have been proposed for use in the vascular system. Typically, the stents are used to hold open a length of blood vessel which has been closed or occluded by some growth within the blood vessel. Balloon expandable stents and self-expanding stents are commercially available and have been used successfully for treatment of a number vascular diseases. Das, Stent, U.S. Pat. No. 5,554,181 (Sep. 10, 1996) shows a wire stent having a number of hoops all attached to a radially disposed spine, all of which may be formed of a single wire. Likewise, Hillstead, Endovascular Stent Apparatus and Method, U.S. Pat. No. 4,856,516 (Aug. 15, 1989). The stents are folded upon a catheter pusher and retained within a catheter sheath before release into the body. These stents must be radially compressed to fit within the catheter sheath, and expand elastically or may be expanded inelastically by a balloon. They are not susceptible to being stretched or elongated in along their long axes to reduce their overall diameter.

SUMMARY

The devices described below allow deformation of a stent or stent like device with the lowest possible profile. The stent is formed of a single wire. Like other stents, the single wire stent has a small diameter configuration to facilitate percutaneous insertion into a blood vessel, and a large diameter configuration which it takes on after insertion into the blood vessel. The stent may include a flow disrupting region disposed intermediate the two ends of the stent. The flow disrupting region is intended to modify flow within the aneurysm and allow the aneurysm to thrombose, shrink and ultimately be clinically resolved. Unlike other stents, the single wire stent delivery system described below does not require that the stent be radially compressed, but instead requires that the stent be longitudinally stretched or deformed to its maximum extent. The result is a small diameter configuration with a diameter that may be as small as two wire thicknesses, and a large diameter configuration that may be as large as necessary to permit retention or the stent within the vessel in which the stent is placed, or maintain patency of the vessel into which the stent is placed. The stent delivery system may be made with the smallest possible outer diameter given the wire size chosen for the stent itself.

BRIEF DESCRIPTION OF THE DRAWINGS

FIG. 3 shows the hoop stent elongated to its maximum extent, in the condition in which it will be loaded onto the delivery catheter FIG. 4 is an isometric view of a flow disrupting device with an axially protruding flow disrupting segment.

FIG. 5 is an isometric view of a flow disrupting device with a conformal flow disrupting segment.

FIG. 6 is an isometric view of a flow disrupting device with an axially protruding flow disrupting coil.

FIG. 7 is a side view of a flow disrupting device with an axially protruding flow disrupting coil.

FIG. 8 is an isometric view of a flow disrupting device with a flow disrupting which does not protrude axially into the aneurysm.

FIG. 9 shows a mandrel for forming the coiled flow disrupting structure

DETAILED DESCRIPTION OF THE INVENTION

Figure 1:
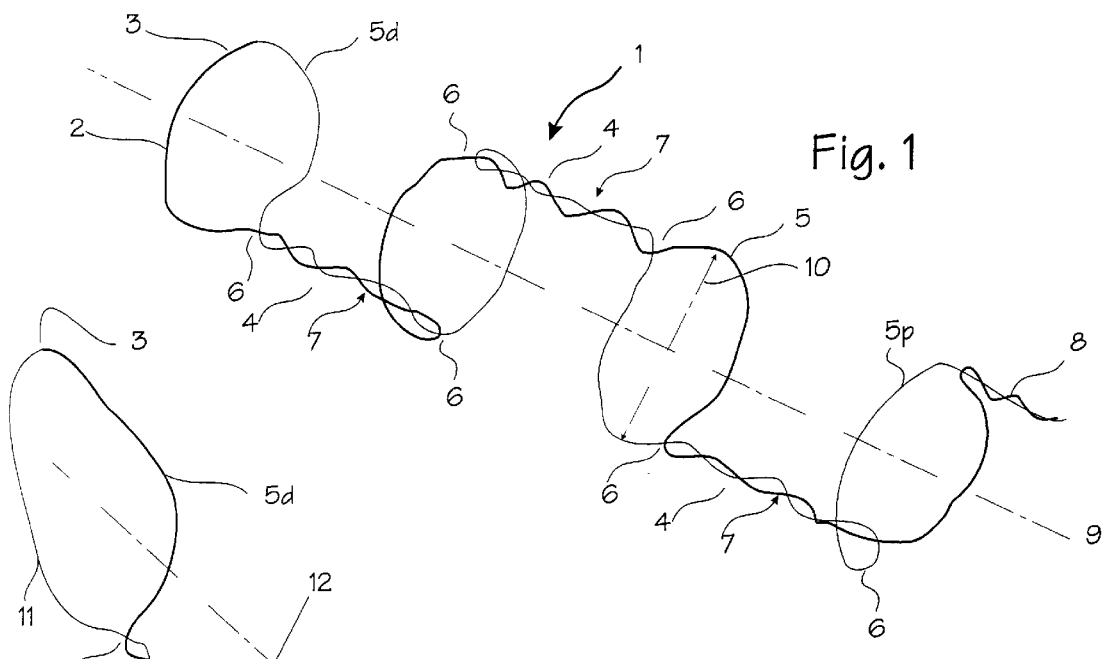
FIG. 1 a perspective view of the stent showing the stent in its expanded state.

FIG. 1 shows the stent in its expanded state. The stent 1 is comprised of a single wire 2 which is folded at a point along the wire, such as mid-point 3 to form a length of double wire comprising two wire segments. Several twisted sections 4 in the double wire are interspersed with several hoops 5 formed by pulling the double wire apart into the hoop shape. The wire can also be made to form coils in place of the hoops. The double wire is then bent at each junction 6 between the twisted sections and the hoops to form an angle of about 90° between each hoop and twisted section. The twisted sections create alternately radially opposed struts, bridges or spines 7 between successive hoops. The free ends 8 of the wire may be twisted into a free spine as shown, or they may be joined together. The hoops in this arrangement are aligned along a common axis 9 which defines the longitudinal axis of the stent, and they are oriented approximately parallel to each other. The stent has an unconstrained diameter defined by hoop diameter 10. The hoops may be all the same overall diameter, or they may be of different diameter, and it may be particularly useful to create the hoops so that the size of the hoops increases from one end of the stent to the other so as to better conform to the tapered blood vessel. The struts may be all the same length or of varying length. Although shown as being formed by intertwining the two wire segments, the struts maybe formed by welding the segments to together, or by shaping the segments to run parallel where the strength of the wire permits. Note that the stent may be formed of two separate lengths of wire, but in this case a free end strut at distal hoop 5d, or a joint provided elsewhere along the stent, may be required.

Figure 2:
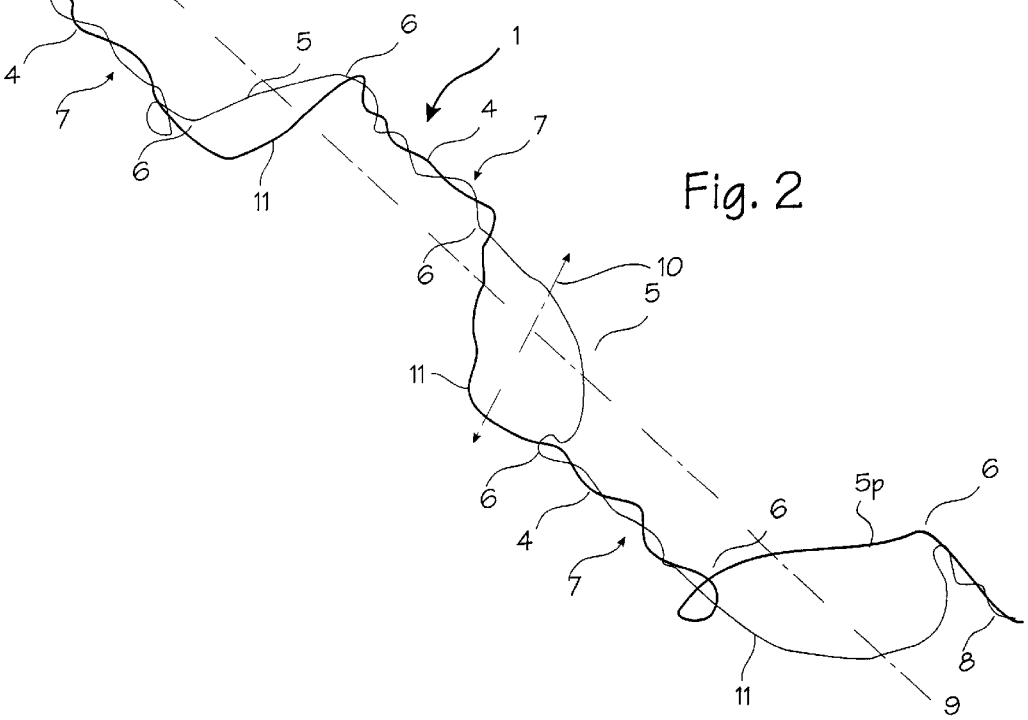
FIG. 2 shows the stent partially stretched out.

FIG. 2 shows the stent partially stretched out. In its partially stretched condition, the hoops 5 have elongated into reclining ellipses 11 oriented at an angle from the longitudinal axis 9 of the stent 1. The angle is intermediate between the longitudinal axis of the stent and the radius 12 of the stent. Thus the overall diameter of the stent has been significantly reduced by stretching along the longitudinal axis. The fact that the struts are not radially aligned permits longitudinal stretching or deformation of every hoop in the stent. As illustrated, each strut is radially opposed to the struts on either side, meaning the each strut is on the opposite side of the stent compared to the preceding or succeeding strut. When the adjacent struts are 180° apart, maximum stretching of the hoops is achieved merely be pulling the ends of the stent. Direct opposition, or opposition of exactly 180°, is not required to obtain the benefit of this construction, and it suffices that the struts not be radially aligned.

FIG. 3 shows the hoop stent elongated to its maximum extent, in the condition in which it will be loaded onto the delivery catheter. In its fully stretched condition, the hoops 5 have elongated into closed or nearly closed ellipses 13 oriented not at an angle from the longitudinal axis 9 of the stent 1, but in line with the longitudinal axis. The angle is close to the longitudinal axis of the stent and perpendicular to the radius 12 of the stent. When stretched completely in the longitudinal direction, the stent has an overall radial thickness of only two wire thicknesses. This provides the thinnest possible insertion diameter for the stent. The stent is loaded in the distal end of a delivery catheter, and delivered percutaneously to the deployment site. The stent may be pushed out of the delivery catheter distal end, or it may be held in place while the delivery catheter is withdrawn. Various other deployment mechanisms may be used, such as the non-sliding sheaths, zip cord sheaths and other embodiments. Where the stent is made of a superelastic alloy (superelastic at body temperature) it will revert to the open hoop configuration of FIG. 1 upon release from the catheter. Where the stent is made of a shape memory alloy with a transition temperature slightly above body temperature, reversion to the memorized shape of FIG. 1 will occur upon injection of warm fluid through the catheter and onto the stent. The reversion will occur between the austenite start temperature As and the austenite finish temperature Af. Typically in this application, the Af would be set to about 30° C. plus or minus 5° C., so full expansion occurs above the normal room temperature and below the normal body temperature. If Af is a degree or so above body temperature, hysteresis may be relied upon to ensure maintenance of superelastic properties when the material is cooled to body temperature.

The stent wires 2 may be made of a shape memory alloy such as nitinol (or other shape memory material), pseudoelastic or superelastic alloy such as nitinol (or other pseudoelastic or superelastic material), spring metal such as stainless steel, or other suitable materials. When made of shape memory nitinol or superelastic nitinol, the stent may be trained to the shape shown in FIG. 1, and will revert to that shape either through shape memory behavior at its chosen transition temperature, or through superelastic behavior at body temperature. The appropriate compositions and training regimens may be used to obtain these characteristics. Spring materials such as stainless steel may be used also, and fabricated so that the shape of FIG. 1 is the relaxed state of the material which is regained elastically after stretching into the shape shown in FIG. 3. As with prior art stents, the stent may also be deployed by inflating a balloon within the stent.

The configuration of the hoop stent shown in FIG. 1 is merely one of the many configurations that may be fabricated of a single wire and deployed in very low profile configurations equal to one or two wire thicknesses. Additional configurations are shown in the remaining figures. These configurations are designed to provide for partial occlusion or flow disruption of aneurysms, which will promote thrombus formation and eventual shrinkage of the aneurysm. While the support structure is similar to the hoop stent discussed above, these stents use the stent structure as a scaffolding mechanism for retaining flow disrupting structures within or about the neck of the aneurysm.

A simple embodiment is shown in FIG. 4. The flow disrupting device 15 comprises a stent body which is formed of a single wire 2, with the strut 7 extending between the distal and proximal hoops. Rather than using overall straight configuration for the strut, the strut is divided into two smaller segments 17 and 18 which are disposed along the strut line. These two struts support a flow disrupting structure 19 which may be integrally formed on the same wire, as shown. The flow disrupting structure 19 in FIG. 4 is a mere camel hump shape which protrudes axially outwardly from the imaginary cylinder defined by the hoops 20l and 20r. The shape may be any irregular shape which protrudes into the aneurysm sac and avoids substantial protrusion into the lumen of the blood vessel.

As the flow disrupting structure may not need to protrude into the aneurysm sac, the flow disrupting device of FIG. 5 may be used where protrusion into the aneurysm sac is contraindicated. The flow disrupting device 21 comprises a stent body 14 which is formed of a single wire 2, with the strut 7 extending between the distal and proximal hoops. As in FIG. 4, the strut is divided into two smaller segments 22 and 23 which are disposed along the strut line. These two struts support a flow disrupting structure which may be integrally formed on the same wire, as shown. The flow disrupting segment 24 differs from that of FIG. 4 in that the shape does not protrude axially outwardly from the imaginary cylinder defined by the hoops 20l and 20r. Instead, the flow disrupting segment comprises a segment 24 of curves that conform to the imaginary cylinder defined by the hoops 20l and 20r, and thus conform generally to the curvature expected in the lumen of the blood vessel in which the device is placed. When placed within a blood vessel so that the flow disrupting segment bridges the mouth of the aneurysm, the disruption of flow will result in eventual thrombosis and diminishment of the aneurysm mass.

Another useful shape for the flow disrupting structure is that of a coil, as illustrated in FIG. 6. Coil tower 26 extends radially outwardly from the struts 27 and 28, and is integrally formed from the single wire 29. The hoops 20l and 20r are formed in the manner as described in reference to FIG. 1. The isometric view shown in FIG. 7 provides another view of the flow disrupting device, with each of the elements being the same as in FIG. 5. The coil tower 26 is sized and dimensioned to fit within an aneurysm sac, while the hoops 20l and 20r are sized and dimensioned to expand into secure contact with the surrounding blood vessel of normal or near normal cylindrical cross section. The struts are of appropriate length to extend from the aneurysm sac to the nearby lumen of normal or near normal cylindrical cross section. FIG. 8 illustrates another embodiment of the flow disrupting device in which the flow disrupting structure comprises a flat coil 30 oriented so that it does not protrude into the aneurysm space. The flat coil may or may not conform to the cylindrical shape of the ideal blood vessel wall.

A mandrel for forming the coiled flow disrupting structure is illustrated in FIG. 9. The mandrel is a tee shaped mandrel with a post for forming the flow disrupting segment and a pair of extensions for forming the struts and hoops. The length of wire is folded over at point C, and the double wire is wrapped around the mandrel tower 31 and held in recessed shaping groove 32. The pin 33 secures the wire to the tower. The doubled wire is then separated so that one wire may be routed to the right side mandrel 34 and wrapped around the mandrel in hoop forming groove 35, while the second wire is routed to the left side mandrel 36 and wrapped in hoop forming groove 37. Each end of single wire may terminate near the endpoint 38 of the hoop forming groove, after making substantially an entire wrap around the mandrel, or each end may return to the center of the device, near the tower for provide additional strength to the struts. The mandrel may be made to disassemble at the junction of the tee once the stent has been shape set on the mandrel.

Two types of aneurysms that permit different deployment methods and different insertion configurations are the saccular side wall aneurysm and the bifurcation aneurysm. In intracranial clinical experience, the bifurcation aneurysm appears predominant, and the basilar tip aneurysm is of great clinical concern. In peripheral vessels, and in the carotid arteries, saccular aneurysms are more common.

Figure 10:
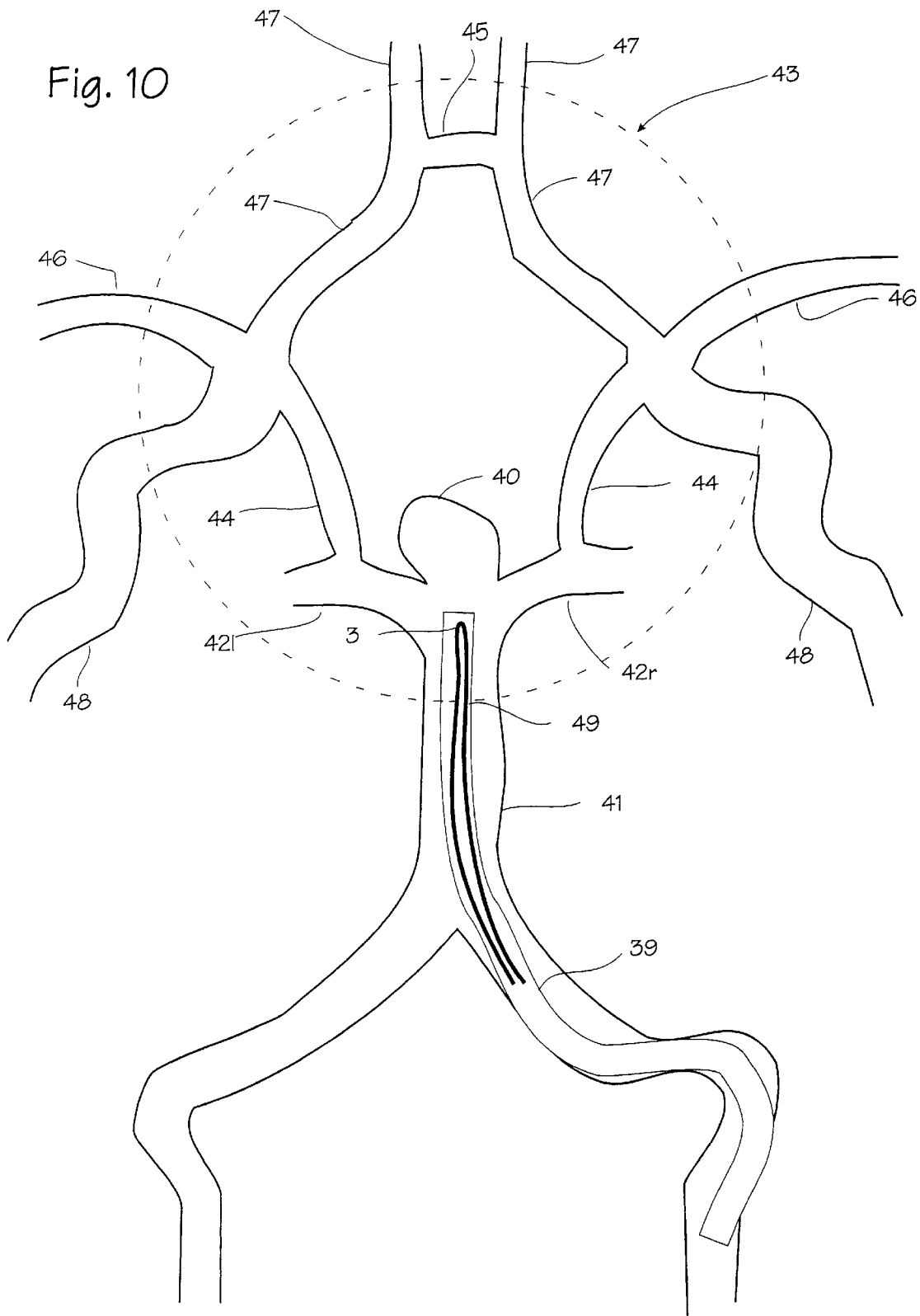
FIG. 10 is a side view of the device of FIG. 7 stretched and inserted within an insertion catheter

A first embodiment of insertion configurations applies to bifurcation aneurysms (although we refer to the bifurcation aneurysm in accordance with the common terminology in the art, it will be apparent that it may be used to treat any end-approachable aneurysm). For insertion into the body, the device may be stretched in the longitudinal direction to form a length of doubled wire, housed within an insertion catheter 39 as illustrated in FIG. 10. For treatment of bifurcation aneurysms, the device is placed within the insertion catheter with the wire bend 3 is disposed at the distal end of the deployment configuration and the wire ends 8 at the proximal end of the deployment configuration. The insertion catheter is inserted into the body according to standard techniques to the point where it is to be deployed. FIG. 10 shows the distal tip of the insertion catheter 39 approaching a basilar tip aneurysm 40. The aneurysm occurs at the bifurcation of the basilar artery 41 into the posterior cerebral arteries 42l and 42r. (This anatomical structure is located in the brain, and is part of the Circle of Willis 43, which is shown for clarity. The other arteries of the Circle of Willis include the posterior communicating arteries 44, the anterior communicating arteries 45, the left and right middle cerebral arteries 46 and the left and right anterior cerebral arteries 47. The internal carotid arteries 48 also supply the Circle of Willis.) The wire bend 3 is placed at the distal end of the deployment configuration so that this point of the device may be inserted into the aneurysm space when the device is pushed or otherwise released from the deployment catheter.

Figure 11:
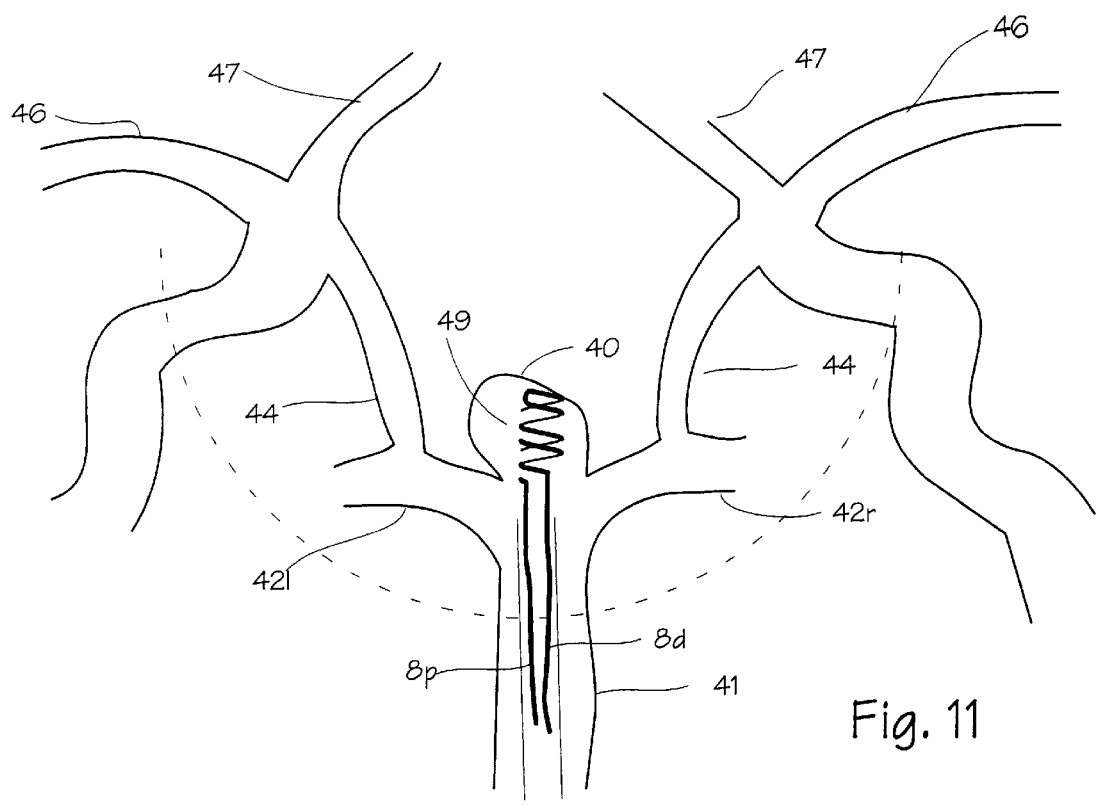
FIG. 11 illustrates the method of placing the device of FIG. 7 within a bifurcation tip aneurysm.
Figure 12:
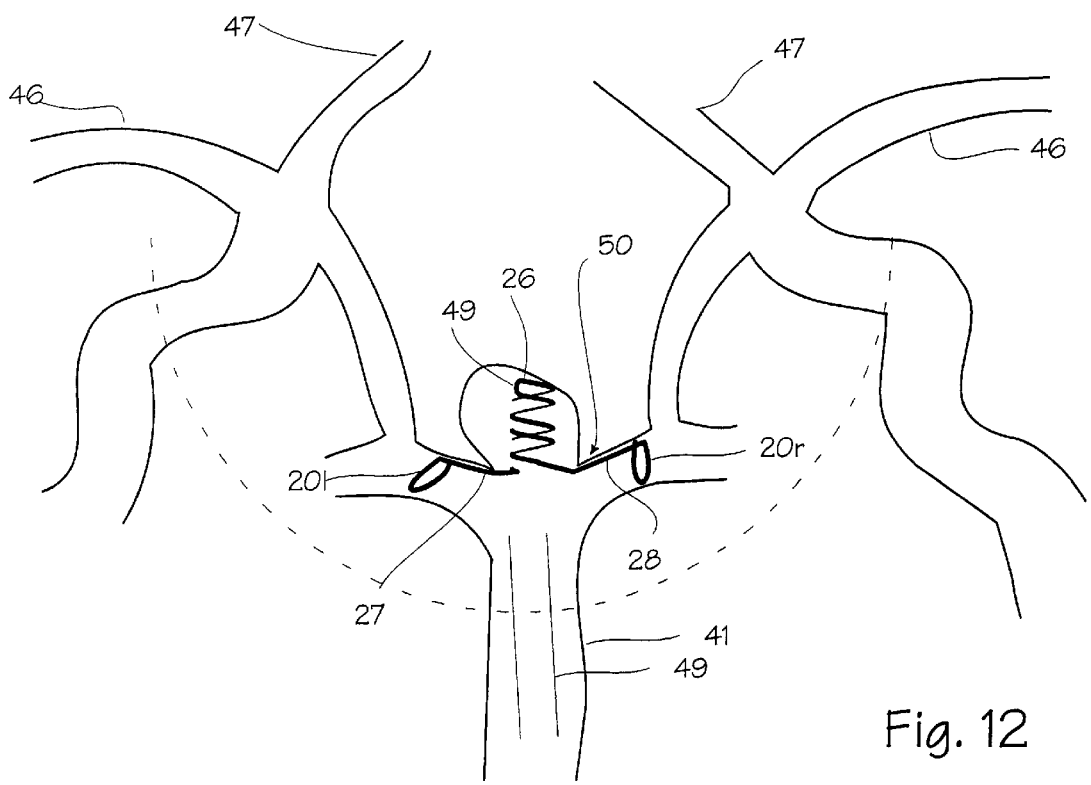
FIG. 12 illustrates the placement of the device of FIG. 7 within a bifurcation tip aneurysm.

Upon release from the catheter, the distal end 49 of the device will revert to its coiled shape. In FIG. 11, the device is partially deployed, and the coiled occluding structure which is not restrained by the catheter has reverted to its coil shape. The further release of the wire ends 8d and 8p will allow the reversion of these portions of the wire to revert into the hoops 20l and 20r and struts 27 and 28. Adjustments to the position of the coil, the hoops or the struts can be made using the insertion catheter to bump and push the parts into place. The hoops should circumscribe the inner wall of the blood vessel, as shown in FIG. 12. After placement, the angle 50 which appears between the struts and the coils is apparent. This angle may be trained into the device before insertion by annealing or training the wire to take on a shape which includes such an acute angle between the struts and the occluding structure of the coil 26. On the other hand, the tension resulting from the 90° angle shown in FIG. 6, upon placement in an environment requiring an installed angle of less that 90°, will result in tension which helps keep the occluding structure 26 firmly held within the aneurysm space.

Figure 13:
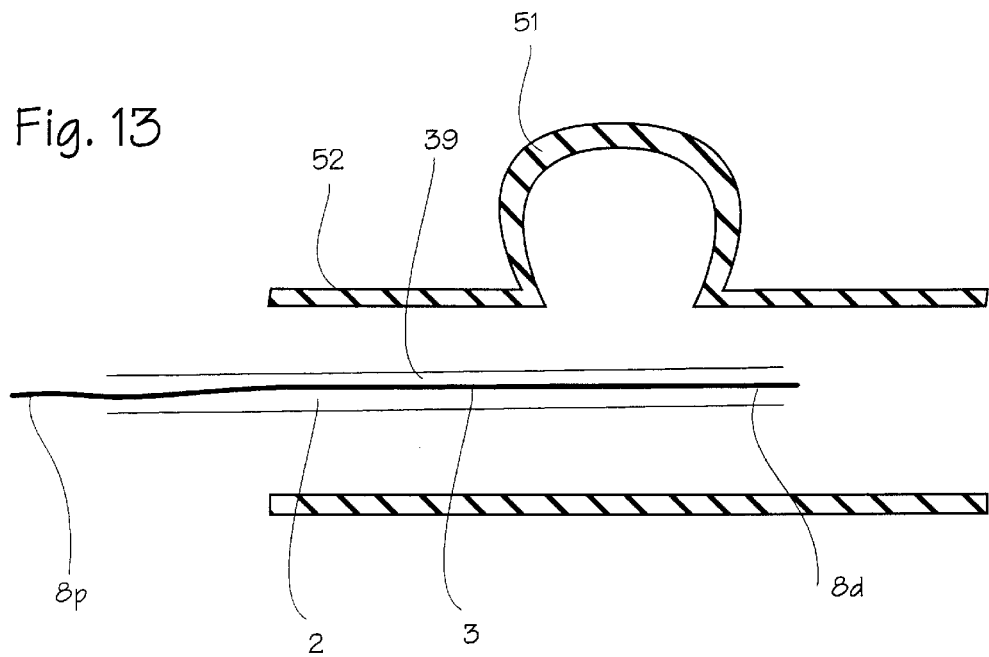
FIG. 13 illustrates the method of placing the device of FIG. 4 within a side wall aneurysm.
Figure 14:
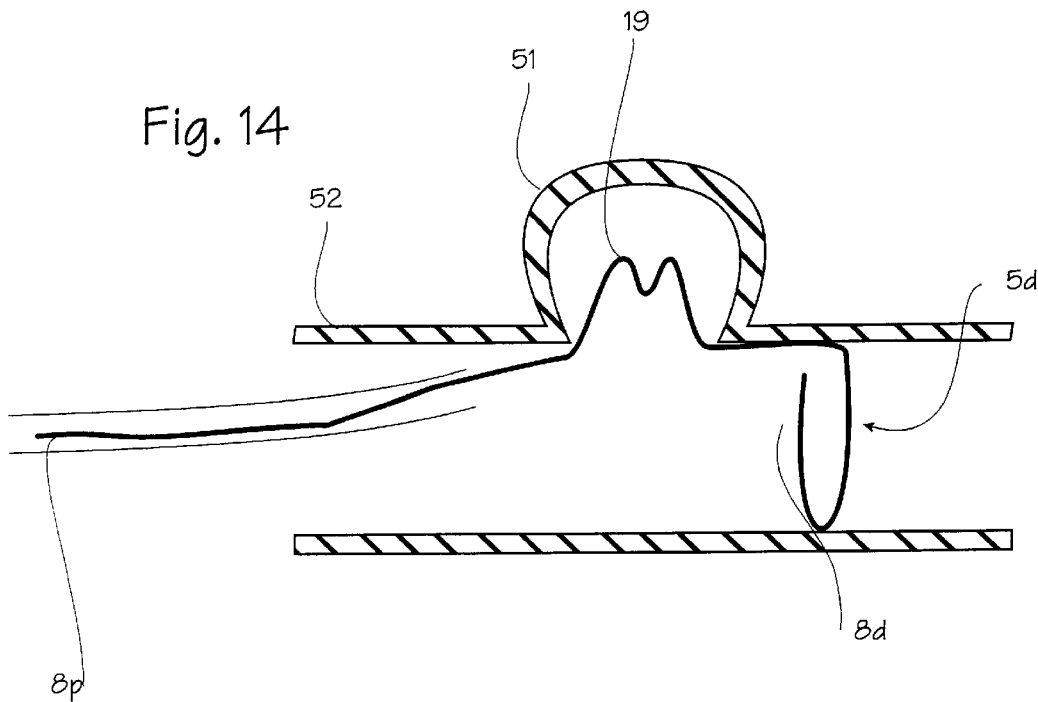
FIG. 14 illustrates the method of placing the device of FIG. 4 within a side wall aneurysm.

For side wall aneurysms, or any aneurysm which can be approached from the side, the occluding device may be inserted fully stretched in a single wire configuration. As shown in FIG. 13, the occluding device 15 of FIG. 4 is stretched into a single long wire 2 with the free ends 8d and 8p of the wire at the distal and proximal ends of the device, and the midpoint 3 in the longitudinal center of the device, housed within the distal end of the insertion catheter 39. To deploy the device, the insertion catheter 39 is inserted into the body and navigated to the site of the aneurysm 51 within the blood vessel 52. As shown in FIG. 13, the distal end of the device (which corresponds to the distal free end 8d) is placed just distal to the aneurysm 51. After the device is properly located, the insertion catheter is removed (by pulling proximally, by peeling or otherwise), the device will revert to its original shape. The distal free end 8d will revert to its memorized hoop shape, and the strut and occluding section will revert to the memorized occluding shape, and finally the proximal free end 8p reverts to its memorized hoop shape. FIG. 14 shows the device partially deployed, with the distal free end 8d reverted into distal hoop 5d and the wire near the midpoint reverted into the flow disrupting structure 19. The proximal free end 8p is shown still within the distal end of the insertion catheter, and will revert to the shape of the proximal hoop 5p upon release.

Each of the occluding device embodiments and the stent embodiments may be controlled with the various methods used for stents and other devices made of nitinol. Nitinol is preferred because its biocompatibility is well proven, and it is available in numerous compositions with well-controlled transition temperatures. (Other shape memory or pseudoelastic materials may be used, and normally elastic stainless steel, Elgiloy, and plastics may be used.) The nitinol used for the device may be used in its shape memory formulation, with a transition temperature just above body temperature, in which case the device may be returned to its memorized shape upon the injection of warm water (just above body temperature). Alternatively, the nitinol used for the device may be used in its pseudoelastic formulations, in which the nitinol is superelastic (also called pseudoelastic) at body temperature, in which case the device will automatically revert to its memorized shape when inside the body. The superelastic device can be superelastically deformed to fit within the insertion catheter so that it can be inserted into the body, and it superelastically reverts to the memorized shape when released from the catheter in the blood stream.

Common among the embodiments of the aneurysm occluding devices is the desire that the occluding structure enhance formation of thrombus within the aneurysm. To enhance this function, the occluding structure may be coated with known thrombogenic materials such as platinum. The hoops and struts which remain outside the aneurysm sac and within the blood stream must remain uncoated with such a thrombogenic coating, and are preferably coated with an anti-thrombogenic coating such as heparin or tin or many other such coatings. Thus the occluding device will have segments of varying thrombo-active coatings, depending on the desired characteristic of each segment. The devices may also be coated with materials such as tantalum, gold and platinum in order to enhance the visibility of the devices under fluoroscopy. The device are clearly visible under intravascular ultrasound which may be used to aid in deployment and proper placement. While the devices will provide for the primary treatment of aneurysms, they may also be used in conjunction with embolic materials and GDC's in order to hold these foreign materials within the aneurysm and prevent their migration from the aneurysm into the blood stream.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for treating a basilar tip aneurysm affecting a bifurcation of the basilar artery, the bifurcation forms the left and right posterior cerebral arteries of a patient, said basilar tip aneurysm having a mouth in communication with the bifurcation, said device comprising:

a first hoop adapted to circumscribe the inner wall of the left posterior cerebral artery on one side of the basilar tip aneurysm;

a second hoop adapted to circumscribe the inner wall of the right posterior cerebral artery on one side of the basilar tip aneurysm;

a first strut comprising length of wire adapted to extend from the first hoop toward the basilar tip aneurysm; and a second strut comprising length of wire adapted to extend from the second hoop toward the basilar tip aneurysm; and a flow occluding structure supported by the first and second struts and adapted to span the mouth of the basilar tip aneurysm;

the device comprises a wire frame structure capable of deformation into a single length of wire; and the device has an insertion configuration and a deployed configuration, said deployed configuration comprising the first hoop, second hoop, first strut, second strut and flow occluding structure, said insertion configuration comprising the wire frame structure deformed into a single length of wire, wherein the wire frame structure in said insertion configuration fits within a catheter for delivery into the body of patient, said wire frame structure reverting to the deployed configuration upon release from the catheter.

2. A device for treating a basilar tip aneurysm affecting a bifurcation of the basilar artery, the bifurcation forms the left and right posterior cerebral arteries of a patient, said basilar tip aneurysm having a mouth in communication with the bifurcation, said device comprising:

a first hoop adapted to circumscribe the inner wall of the left posterior cerebral artery on one side of the basilar tip aneurysm;

a second hoop adapted to circumscribe the inner wall of the right posterior cerebral artery on one side of the basilar tip aneurysm;

a first strut comprising length of wire adapted to extend from the first hoop toward the basilar tip aneurysm; and a second strut comprising length of wire adapted to extend from the second hoop toward the basilar tip aneurysm; and a flow occluding structure supported by the first and second struts and adapted to span the mouth of the basilar tip aneurysm;

the device comprises a wire frame structure capable of deformation into a length of double wire bent at a midpoint of the wire; and the device has an insertion configuration and a deployed configuration, said deployed configuration comprising the first hoop, second hoop, first strut and second strut and flow occluding structure, said insertion configuration comprising the wire frame structure deformed into a length of double wire bent at a midpoint of the wire, wherein the wire frame structure in said insertion configuration fits within a catheter for delivery into the body of patient, said wire frame structure reverting to the deployed configuration upon release from the catheter.

3. A system for treating a basilar tip aneurysm affecting a bifurcation of the basilar artery the bifurcation forms the left and right posterior cerebral arteries of a patient, said basilar tip aneurysm having a mouth in communication with the bifurcation, said left and right posterior cerebral arteries having an inner wall, said system comprising a flow disrupting device and an insertion device, wherein:

said flow disrupting device has a deployed shape which comprises:

a first hoop adapted to circumscribe the inner wall of the left posterior cerebral artery on one side of the aneurysm;

a second hoop adapted to circumscribe the inner wall of the right posterior cerebral artery on one side of the aneurysm;

a strut connecting the first and second hoops; and a flow occluding structure supported by the strut and capable of being aligned with the aneurysm to disrupt the flow of blood into the aneurysm;

wherein the flow disrupting device comprises a wire frame structure capable of deformation into straight line configuration; and said insertion device comprises:

a catheter having a lumen at its distal end, said catheter being sized and dimensioned to allow insertion of the catheter into the body to the bifurcation of the basilar artery and the left and right posterior cerebral arteries, said lumen having an internal diameter sufficient to house the flow disrupting device in its straight line configuration;

wherein the flow disrupting device may be deformed into its straight line configuration and inserted into the lumen at the distal end of the catheter for insertion into the body, and the flow disrupting device resiliently reverts to the deployed shape upon release from the lumen at the distal end of the catheter.

4. The device according to claim 3, wherein the flow occluding structure is adapted to protrude into the basilar aneurysm.

5. The device according to claim 3, wherein the flow occluding structure comprises a coil which is adapted to protrude into the aneurysm.

6. The device according to claim 3, wherein the flow occluding structure comprises a length of wire which is adapted to protrude into the aneurysm.

7. The device of claim 3 wherein the flow occluding structure consists of a segment of the strut adapted to span the mouth of the aneurysm without protruding into the aneurysm.

8. The device of claim 3 wherein the flow occluding structure consists of a curved segment of the strut, said curved segment adapted to span the mouth of the aneurysm without protruding into the aneurysm.

9. The device according to claim 3, wherein the flow occluding structure comprises a curved length of wire which is adapted to conform to the mouth of the aneurysm and does not protrude into the aneurysm.

10. The device according to claim 3, wherein the flow occluding structure comprises an elastic, superelastic, or shape memory material.

11. The device according to claim 3, wherein the insertion configuration comprises the wire frame structure deformed into a single length of wire.

12. The device according to claim 3, wherein the insertion configuration comprises the wire frame structure deformed into a doubled length of wire.

* * * * *